April 16, 1968 A. PERRY Plant Pat. 2,804
ROSE PLANT
Filed Dec. 5, 1966
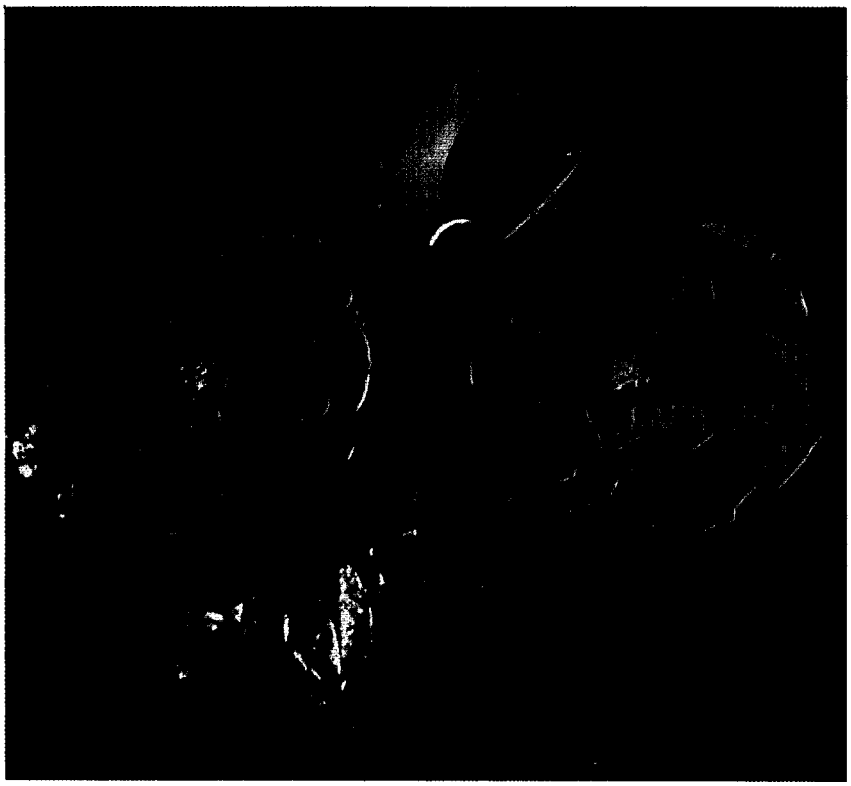
INVENTOR.
ANTHONY PERRY
BY J. F. Cuneo
ATTORNEY

United States Patent Office

Plant Pat. 2,804
Patented Apr. 16, 1968

2,804
ROSE PLANT

Anthony Perry, Garden Grove, Calif., assignor to Henry A. Conklin, McFarland, Calif.

Filed Dec. 5, 1966, Ser. No. 599,330
1 Claim. (Cl. Plt.—20)

This invention relates to a new and distinct variety of rose plant that is generally classified as a hybrid grandiflora.

This new variety resulted from cross-breeding Queen Elizabeth, a patented rose, United States Plant Patent No. 1,259, with Circus, a patented rose, United States Plant Patent No. 1,382, after numerous experiments conducted by me at Garden Grove, Calif. The original plant was produced by me in June of 1959, using Queen Elizabeth as the seed parent and Circus as the pollen parent.

The flowers produced by the new variety of rose plant are scarlet to red in color and are sometimes borne on a single stem but usually three or four blooms are borne on a stem from six to twelve inches in length. The flowers are produced in abundance during the growing season that generally extends from February to and often through November when the plant is grown in the coastal region of southern California. The plant forms a medium-sized bush that is predominantly upright with the bushes varying from three to five feet in height.

In comparing the new variety with its seed parent Queen Elizabeth it is observed that the foliage is somewhat similar but this plant is not quite as tall as its seed parent. The blooms of the new variety are entirely different in color from those of the seed parent which are pink, while those of the new variety are scarlet to red in color.

When compared to its pollen parent the new variety forms a plant that is much taller than Circus and the blooms are of an entirely different color. The blooms of the new variety are from scarlet to red depending on the age of the bloom, while those of the pollen parent are best described as multicolor with the yellow being the principal coloration. The plant is quite hardy and exhibits a vigorous upright growth which sometimes will reach five feet in height.

The new variety belongs to the outdoor bush type and is used for garden ornamentation as well as cut flowers. The plant has been reproduced asexually by budding performed in Garden Grove, Calif, as well as in McFarland, Calif. The resulting plants and the flowers reproduced true with all of the distinguishing characteristics being transmitted through the succeeding propagations of the variety; the plant will not reproduce true from seed.

The accompanying illustrating in full color shows a typical specimen of the blooms produced by this new variety. The colors shown are as true as it is possible to reproduce them by using this type of illustrating color process.

A detailed description of the new variety of rose plant follows and in order to facilitate identification of the important colors described in the specification, the designations adopted by the British Horticultural Colour Charts have been followed.

The new rose belongs to the outdoor bush type and is of the so-called hybrid grandiflora class. Its flaming red blooms are very colorful and are particularly desirable for cut flowers and as a garden ornamentation.

*The flower*

Locality where grown and observed: Garden Grove, Calif.; McFarland, Calif.

Flowers borne: The flowers are borne generally with three or four blooms on a stem that varies from six to twelve inches in length. Occasionally a single bloom is found on a stem.

Number of blooms: When raised outdoor the plant produces an abundance of blooms, there being from twenty to fifty blooms on a plant at one time.

Continuity: The plant blooms usually in the latter part of February and continues to bloom to November and in mild years will bloom through November. Extremely warm weather has a tendency of reducing the number and size of the blooms.

Fragrance: This variety produces a rose that has what is best described as a spice fragrance.

Bud:

*Peduncle.*—Length—from one and one-half to two inches. Color—green.

*Before calyx breaks.*—Size—usually about three-quarters of an inch in diameter. Form—the bud is best described as ovid in form.

*As calyx breaks.*—Color—scarlet. Sepals: shape—generally spear-shaped with rounded base; size—the sepals are usually one and one-half inches long.

*As first petal opens.*—Size—the petals are approximately two inches long and about the same width. Color—the petals are Scarlet 19 and gradually shade to Chinese Yellow 606 at the base of the petal. Form—petals are roughly orbiculate.

Bloom:

*Size.*—The blooms are from two and one-half to three and one-half inches across.

*Petalage.*—The number of petals are approximately thirty.

*Form.*—Globular with a high center.

*Petals.*—Shape—the petals are substantially round at the tip with the base slightly acute. Size—matured petals are approximately two inches across. Color—the petals when fully opened are Scarlet 19 and as they grow older they become Ruby Red 827. The petals shade to Chinese Yellow 606 at the base tip. Texture—the texture of the petals is leathery.

*General color effect.*—The general color effect is a ruby red flower.

*Behaviour.*—The petals drop off clean. The bloom has a medium rate of opening. Warm weather has the effect of producing stunted flowers.

*Flower longevity.*—The flowers last from five to seven days.

*Reproductive organs*

Stamens: Average in number.

Filaments:

*Length.*—Filaments are about ¼" in length.

*Color.*—Filaments are golden in color.

Anthers: Anthers are not prominent. Color—golden yellow.

Pollen:

*Quantity.*—Moderate.

*Color.*—Golden yellow.

Pistils: Number—numerous.

Styles: Prominent. Size and arrangement—medium.

Stigma: Color—golden.

Ovaries: Visible when flower is torn open. These are golden in color.

Hips:

*Length.*—Average, one-half to three-quarters of an inch.

*Form.*—Oblong.

*Color.*—Bronze green.

Seeds: Seeds are large but do not set freely.

*The plant*

Foliage: Compound, odd pinnate leaves having an average of five leaflets ordinarily.

*Quantitiy.*—Average.

*Leaflets.*—Shape—leaflets are generally ovate with a tip that is slightly acuminate; the base of each leaflet is obtuse to truncate; the margin of the leaflets is serrulate. Size—the leaflets are usually from one and one-half to two inches in length. Color: upper side—Spinach Green o960; lower side—Spinach Green o960/2.

*Young leaflets.*—Color—young leaflets have approximately the same color as the mature leaflets but these have a reddish coloration that disappears as the leaflets mature.

*Type.*—Imparipinnate.

*Stipules.*—Stipules are not prominent and what few do appear are about ¼″ in length.

Growth: Habit and height—the plant is vigorous, upright and well branched; the bushes range from 3½ to 5 feet in height.

Canes: The diameter of the canes will average one-half inch.

Main stems: *Length.*—Sixteen to eighteen inches.

*Color.*—Bronze green.

Prickles (large): Size and number—the large prickles are from three eights to one-half inches long and are medium in number.

Prickles (small): None.

Branches:

*Color.*—Bronze green.

*Habit.*—Upright predominantly.

*Hair.*—None.

*Thorns.*—*Number and size*—thorns are moderate in number and are medium spaced; these vary from ⅜″ to ½″ in length.

*Small prickles.*—None.

New shoots:

*Color.*—Light green.

*Large prickles; small prickles.*—Large prickles present; no small prickles.

Having described my invention, I claim:

1. The new and distinct variety of rose plant of the class designated as hybrid grandiflora, substantially as herein shown and described, characterized particularly as to novelty by its very colorful, globular, highcentered medium sized blooms that range in color from Scarlet to Ruby Red, said blooms borne from three to four on a stem, by the spicy fragrance of the flowers, and by the medium height, vigorous, upright, well branched growth habit of the plant.

No references cited.

ROBERT E. BAGWILL, *Primary Examiner.*